United States Patent [19]

McClune

[11] Patent Number: 4,828,983

[45] Date of Patent: May 9, 1989

[54] USE OF PHENOLS AND ANILINES TO INCREASE THE RATE OF PEROXIDASE CATALYZED OXIDATION OF LEUCO DYES

[75] Inventor: Gregory J. McClune, Rochester, N.Y.

[73] Assignee: Eastman Kodak Company, Rochester, N.Y.

[21] Appl. No.: 884,329

[22] Filed: Jul. 10, 1986

[51] Int. Cl.⁴ .................. C12Q 1/28; G01N 33/58; G01N 33/52; G01N 33/53

[52] U.S. Cl. .......................... 435/7; 435/10; 435/11; 435/14; 435/17; 435/25; 435/28; 430/223; 422/56

[58] Field of Search .............. 435/7, 10, 14, 25, 11, 435/17, 28, 810; 436/904; 430/223; 422/56, 57

[56] References Cited

U.S. PATENT DOCUMENTS

| | | | |
|---|---|---|---|
| 4,089,747 | 5/1978 | Bruschi | 195/99 |
| 4,260,679 | 4/1981 | Tsuda et al. | 435/28 |
| 4,302,534 | 11/1981 | Halmann et al. | 435/6 |
| 4,424,150 | 1/1984 | Khanna | 260/112 |
| 4,504,413 | 3/1985 | Khanna | 260/112 |
| 4,521,511 | 6/1985 | Stout | 435/28 |
| 4,729,950 | 3/1988 | Kricka et al. | 435/7 X |

FOREIGN PATENT DOCUMENTS

| | | |
|---|---|---|
| 864669 | 9/1978 | Belgium . |
| 116454 | 8/1984 | European Pat. Off. . |
| 57-94653 | 6/1982 | Japan . |
| 57-144998 | 9/1982 | Japan . |
| 57-174099 | 9/1982 | Japan . |

OTHER PUBLICATIONS

Thorpe et al., *Clin. Chem.* 31(8), pp. 1335–1341, (1985).
Halliwell, *Planta*, 140, pp. 81–88, (1978).
Mäder et al., *Plant Physiol*, 70, pp. 1128–1134, (1982).
Brooks, *Biochem. Biophys. Res. Com.*, 116(3), pp. 916–921, (1983).
Kenten et al., *Biochem*, 50, pp. 29–34, (1951); 46, pp. 67–73, (1949).

*Primary Examiner*—Robert J. Warden
*Assistant Examiner*—Carol A. Spiegel
*Attorney, Agent, or Firm*—J. Lanny Tucker

[57] ABSTRACT

Certain phenols and anilines can be used as electron transfer agents to increase the rate of oxidation of leuco dyes by peroxidase. These phenols and anilines can react with hydrogen peroxide in the presence of peroxidase to provide intermediates which have higher oxidation potentials than the slowly oxidized substrates, e.g. the leuco dyes. These phenols and anilines can be used to advantage in both solution and dry assays of various analytes. They are particularly useful for the determination of an immunologically reactive ligand in an immunoassay.

26 Claims, No Drawings

USE OF PHENOLS AND ANILINES TO INCREASE THE RATE OF PEROXIDASE CATALYZED OXIDATION OF LEUCO DYES

FIELD OF THE INVENTION

The present invention relates generally to clinical chemistry. In particular, it relates to analytical compositions, elements and methods useful for the determination of an analyte in biological fluids. For example, the present invention can be used in an immunoassay.

BACKGROUND OF THE INVENTION

It is well known to perform a quantitative or qualitative analysis of an aqueous liquid by contacting that liquid with a combination of reagents capable of yielding a detectable product in proportion to the concentration of the analyte in the liquid. As used herein, this combination of reagents is termed an interactive composition which is capable of chemical reactivity, catalytic activity, or any other form of chemical or physical interaction that can result in the ultimate production of a change that is detectable with suitable procedures and equipment.

One type of useful assay utilizes enzymatic reactions wherein the analyte, upon contact with the appropriate reagents, reacts with oxygen in the presence of a suitable enzyme to produce hydrogen perozide in proportion to the concentration of the analyte. A detectable product is then produced by the reaction of hydrogen peroxide in proportion to the concentration of the analyte in the tested liquid. Peroxidase is generally used in such assays to catalyze the oxidation of interactive composition by hydrogen peroxide.

Peroxidase can be used for diagnostic determinations of various analytes such as glucose, triglycerides, uric acid, cholesterol, creatine kinase, etc. and can be used as a label in ligand analogs used in the determination of immunologically reactive species (i.e. immunoassays). Such determinations can be carried out in solution or in dry analytical elements, such as those described in U.S. Pat. Nos. 3,992,158 (issued Nov. 16, 1976 to Przybylowicz et al), 4,089,747 (issued May 16, 1978 to Bruschi) and 4,258,001 (issued Mar. 24, 1981 to Pierce et al).

The rate of reaction of various substrates with peroxidase varies over many orders of magnitude. In some instances, where the reaction proceeds slowly, a large amount of peroxidase is used to increase the reaction rate. However, the use of large amounts of peroxidase to increase the rate of reaction cannot be used in certain assays. For example, enzyme immunoassays using a peroxidase-labeled ligand analog have become important for determining a drug, antigen or other immunologically reactive compound. In such assays, a large amount of peroxidase cannot be added to increase the enzymatic reaction rate.

E.P. Publication No. 116,454 (published Aug. 22, 1984) describes an immunoassay using peroxidase, an oxidant (e.g., hydrogen peroxide), a chemiluminescent substrate and a phenol as a sensitivity enhancer. These enhancers allegedly increase the sensitivity of the chemiluminescent assay thereby providing a higher quantity of measurable light in the assay. No leuco dyes are used in a chemiluminescent assay. There is no suggestion in this reference that certain phenols or anilines could act as electron transfer agents to increase the rate of oxidation of leuco dyes. Chemiluminescent assays have the disadvantages of (1) requiring specialized equipment, (2) being excessively sensitive to sample volume changes, (3) often requiring relatively high pH, and (4) exhibiting poor assay precision. Hence, there are sufficient reasons for avoiding chemiluminescent assays if possible.

Useful assays utilizing triarylimidazole leuco dyes are described in U.S. Pat. No. 4,089,747, noted above. However, it has been observed in such assays that the oxidation of the leuco dye by peroxidase is relatively slow. Large amounts of peroxidase are needed to increase the rate of reaction, but using increased amounts of peroxidase is often undesirable or impractical for economic reasons or because increased amounts adversely affect the assay, e.g. when peroxidase is used as a label in immunoassays. Hence, it would be desirable to be able to increase the reaction rate of peroxidase catalyzed oxidation of leuco dyes without having to increase the amount of peroxidase.

SUMMARY OF THE INVENTION

The problems noted above are overcome with an analytical composition comprising: peroxidase or a peroxidase-labeled analog of an immunologically reactive ligand, a leuco dye which is capable of providing a detectable dye in the presence of peroxidase and hydrogen peroxide, and a phenol or aniline electron transfer agent which is capable of reacting with hydrogen peroxide in the presence of peroxidase to provide an intermediate compound which has a higher oxidation potential than the leuco dye.

This invention also provides an analytical element comprising an absorbent carrier material containing: peroxidase or a peroxidase-labeled analog of an immunologically reactive ligand, a leuco dye which is capable of providing a detectable dye in the presence of peroxidase and hydrogen peroxide, and a phenol or aniline electron transfer agent which is capable of reacting with hydrogen peroxide in the presence of peroxidase to provide an intermediate compound which has a higher oxidation potential than the leuco dye.

In a preferred embodiment, an analytical element comprises a support having thereon a registration zone and a porous spreading zone, the element further comprising, independently in any of the zones, peroxidase or a peroxidase-labeled analog of an immunologically reactive ligand, a leuco dye which is capable of providing a detectable dye in the presence of peroxidase and hydrogen peroxide, and a phenol or aniline electron transfer agent which is capable of reacting with hydrogen peroxide in the presence of peroxidase to provide an intermediate compound which has a higher oxidation potential than the leuco dye.

A method for the determination of an analyte comprises the steps of:

A. contacting a sample of a liquid suspected of containing an analyte with:

peroxidase or a peroxidase-labeled analog of an immunologically reactive ligand, a leuco dye which is capable of providing a detectable dye in the presence of peroxidase and hydrogen peroxide, and a phenol or aniline electron transfer agent which is capable of reacting with hydrogen peroxide in the presence of peroxidase to provide an intermediate compound which has a higher oxidation potential than the leuco dye, and B. determining the detectable dye as a result of the presence of the analyte.

The present invention provides a means for increasing the reaction rate of leuco dye oxidation by peroxidase catalysis when used in combination with a leuco dye. This advantage is achieved by using certain phenols or anilines with peroxidase and the leuco dye in a solution or dry assay. These phenols and anilines must be capable of acting as electron transfer agents, i.e. capable of reacting with hydrogen peroxide in the presence of peroxidase to provide an intermediate compound which has a higher oxidation potential than the leuco dye. This invention combines the advantages obtained with use of leuco dyes which provide high extinction dyes with the advantage of very rapid reaction rates.

DETAILED DESCRIPTION OF THE INVENTION

The present invention relates to the determination (qualitative or quantitative measurement) of a chemical or biological substance, termed an analyte herein, in aqueous liquids. In particular, the invention can be used to assay biological fluids of either animals or humans. Such fluids include, but are not limited to, whole blood, plasma, sera, lymph, bile, urine, spinal fluid, sputum, perspiration and the like as well as stool secretions. It is also possible to assay fluid preparations of human or animal tissue such as skeletal muscle, heart, kidney, lungs, brains, bone marrow, skin and the like.

Hydrogen peroxide can be determined with this present invention. In addition, the invention can be used to determine analytes which are capable of producing hydrogen peroxide, i.e. they can participate in one or more reactions which produce hydrogen peroxide in the presence of suitable interactive compositions. Analytes which can be determined in this manner include glucose, triglycerides, uric acid, cholesterol, galactose, amino acids, creatine kinase, pyruvate, and others known to one skilled in the art. This invention is particularly useful for the determination of glucose, triglycerides, uric acid, cholesterol and creatine kinase.

In a preferred embodiment, the present invention is useful for the determination of an immunologically reactive ligand which is a substance that will complex specifically with a corresponding receptor. Such ligands include, but are not limited to, antigens, haptens, antibodies, toxins, hormones, therapeutic drugs, natural and synthetic steroids, proteins, viruses, bacteria, peptides, nucleotides, etc. In this embodiment, the ligand to be determined and the corresponding labeled ligand analog compete for a fixed amount of common reactant. This reactant which specifically recognizes the ligand and ligand analog and reacts to form complexes with them is referred to herein as the receptor.

The analytical composition of this invention comprises peroxidase or a peroxidase-labeled ligand analog. Either synthetic or naturally occurring (i.e. obtained from plant, milk, bacteria and other known sources) peroxidases can be used. These materials are generally available commercially or readily extracted from available sources. The peroxidase-labeled ligand analogs useful in this invention are prepared using any suitable technique known to one skilled in the art. Generally, they are prepared by covalently binding (with or without a linking group) the peroxidase label to the ligand molecule which may be modified in any suitable way to achieve the binding.

Any suitable leuco dye can be used in the practice of this invention as long as it is capable of providing a detectable dye when oxidized in the presence of peroxidase and hydrogen peroxide.

Examples of useful leuco dyes include, but are not limited to, imidazole derivatives such as those described in U.S. Pat. No. 4,089,747 (noted above) and references noted therein, E.P. Application No. 122,641 (published Oct. 24, 1984) and Jap. Patent Publication No. 58(1983)-045,557, and the triarylmethanes described, for example, in U.S. Pat. No. 4,670,385 (issued Jun. 2, 1987 to Babb et al). Now U.S. Pat. No. 4,670,385.

The triarylimidiazoles of U.S. Pat. No. 4,089,747 are preferred in the practice of this invention. These leuco dyes generally have the formula

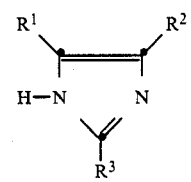

wherein $R^1$, $R^2$ and $R^3$ are independently an organic group such that at least one of them is an ortho or para hydroxy-substituted aryl group of up to 18 carbon atoms, and the other two groups being chosen such that the oxidation potential of the compound is within the range of from about $-70$ mV to about $+100$ mV as measured by cyclic voltometry against a standard calomel electrode using a carbon based electrode. Further details of these preferred leuco dyes and the technique of measuring the oxidation potential are provided in U.S. Pat. No. 4,089,747, noted above.

Phenols and anilines useful in the practice of this invention are those which act as electron transfer agents in the oxidation of the leuco dye to provide a detectable dye. These phenols and anilines react with hydrogen peroxide in the presence of peroxidase to provide intermediate compounds having a higher oxidation potential than the leuco dye used in the assay. The reaction of the phenol or aniline, hydrogen peroxide and peroxidase must be faster than the reaction of the leuco dye, hydrogen peroxide and peroxidase, and the intermediate formed thereby must react rapidly with the leuco dye or other slowly oxidized substrates. Preferably, the first reaction is at least 2 times faster than the second reaction.

Therefore, a simple test can be carried out to determine if a given phenol or aniline is useful in this invention: the rates of oxidation of leuco dye are compared in the presence or absence of a phenol or aniline. If the rate in the presence of a phenol or aniline is faster by at least 2 times, the phenol or aniline is useful in the practice of this invention. It should be understood that a phenol or aniline useful in this invention may not be useful with every leuco dye, but a skilled worker in the art can readily determine which leuco dye and phenol or aniline are useful in the practice of this invention.

Representative phenols useful in this invention include: p, p'-biphenol 4'-hydroxyacetanilide, p-methoxyphenol, chlorphenol red, p-cresol, m-methoxphenol, vanillin, 4-chloro-3,5-dimethylamino-phenol, homovanillic acid, p-hydroxybenzoic acid, p-hydroxyphenylacetic acid, o-methoxyphenol, phenol, resorcinol, and methyl-p-hydroxybenzoate. Useful anilines include: p-anisidine, 4'-aminoacetanilide, p-hydroxy-N, N-dimethylaniline and o-phenylenedi-amine. Phenols and anilines selected from the group consisting of p, p'-biphenol 4'-hydroxyacetanilide, p-methoxyphenol, p-anisidine and 4'-aminoacetanilide are preferred, and 4'-hydroxyacetanilide is most preferred.

As noted above, an interactive composition can be used with the analytical composition of this invention in order to determine an analyte other than hydrogen peroxide. An interactive composition comprises one or more reagents which react with the analyte to produce hydrogen peroxide. Suitable interactive compositions are known to one skilled in the art. For example, an interactive composition for the determination of uric acid includes uricase, and an interactive composition for the determination of glucose includes glucose oxidase. An interactive composition for the determination of cholesterol includes cholesterol oxidase and cholesterol ester hydrolase.

The analytical composition of this invention can also be used to determine an immunologically reactive ligand using a ligand analog which comprises a ligand covalently bound to a suitable label. As noted above, in one embodiment, that label is peroxidase. In other embodiments, the label is an enzyme other than peroxidase e.g. glucose oxidase, galactose oxidase, etc. that participates in the conversion of the analyte to hydrogen peroxide and the leuco dye to a detectable dye. These ligand analogs can be prepared by techniques known to one skilled in the art. Preferably, the ligand analog comprises glucose oxidase or peroxidase.

The analytical composition of this invention can also include other addenda commonly included for assays, e.g. buffers, surfactants, etc. in amounts known in the art.

The analytical composition and method of this invention are adaptable to both solution and dry assays. In a solution assay for analytes other than immunologically reactive ligands, the analytical composition and the interactive composition (if included) are contacted and mixed with a liquid sample suspected of containing the analyte in a suitable container (e.g. test tube, petri dish, beaker, cuvette, etc.). The resulting solution may be incubated for a short period of time at a temperature up to 40° C., and the detectable dye resulting from the presence of the analyte is measured using suitable detection equipment and procedures.

In an immunoassay of this invention, either the bound (complexed) or unbound (uncomplexed) fraction of the labeled ligand analog can be measured. Physical separation of bound and unbound ligand analog, if desired, can be accomplished with any suitable technique. In a solution immunoassay, the ligand analog, appropriate receptor and the liquid sample suspected of containing the ligand are mixed in a container as described above. After complexation, the sample is evaluated by measuring the bound or unbound ligand analog using suitable equipment and procedures.

In a solution assay, the amount of the leuco dye used will depend upon the extinction coefficient of the resulting dye. The appropriate amounts can be readily determined. Generally, the leuco dye is present in a concentration of at least about $4 \times 10^{-7}$, and preferably from about $2 \times 10^{-6}$ to about $1 \times 10^{-4}$, molar. Similarly, peroxidase is present in an amount sufficient to oxidize the leuco dye to provide a detectable signal. Generally, peroxidase is present in an amount of at least about $10^{-13}$ molar. The advantage of this invention is that less peroxidase can be used in many assays because the phenol or aniline described herein enhances the reaction rate of the enzyme. The amount of phenol or aniline used in the assay can be varied depending upon the leuco dye used and the rate of its oxidation to a dye. Generally, however, it is present in an amount of at least about $10^{-6}$, and preferably from about $10^{-4}$ to about $10^{-2}$, molar.

In a solution immunoassay, the ligand analog is generally present in a concentration of at least about $10^{-11}$, and preferably from about $10^{-10}$ to about $10^{-7}$, molar. The corresponding receptor (e.g. antibodies) are generally present in an amount of at least about $10^{-8}$, and preferably from about $10^{-8}$ to about $10^{-3}$, molar.

The method of this invention can also be practiced with a dry analytical element. The simplest element can be composed of an absorbent carrier material, e.g. a thin sheet of a self-supporting absorbent or bibulous material, such as filter paper or strips, which contains the analytical composition of this invention. The element can be divided into two or more discrete zones with different components of the composition incorporated into individual zones of the carrier material. Such elements are known in the art as test strips, diagnostic elements, dip sticks, diagnostic agents and the like.

Useful absorbent carrier materials are insoluble and maintain their structural integrity when exposed to water or biological fluids such as whole blood or serum. Useful elements can be prepared from paper, porous particulate structures, porus polymeric films, cellulose, glass fibers, woven and nonwoven fabrics (synthetic and nonsynthetic) and the like. Useful materials and procedures for making such elements are well known in the art as exemplified in U.S. Pat. Nos. 3,092,465 (issued June 4, 1963 to Adams et al), 3,802,842 (issued Apr. 9, 1974 to Lange et al), 3,915,647 (issued Oct. 28, 1975 to Wright), 3,917,453 (issued Nov. 4, 1975 to Milligan et al), 3,936,357 (issued Feb. 3, 1976 to Milligan et al), 4,248,829 (issued Feb. 3, 1981 to Kitajima et al), 4,255,384 (issued Mar. 10, 1981 Kitajima et al), 4,270,920 (issued June 2, 1981 to Kondo et al) and 4,312,834 (issued Jan. 26, 1982 to Vogel et al).

Preferably, the absorbent carrier material of the dry analytical element of this invention is a porous spreading zone. This zone can be self-supporting (i.e. composed of a material rigid enough to maintain its integrity), but preferably it is carried on a separate support. Such a support can be any suitable dimensionally stable, and preferably, nonporous and transparent (i.e. radiation transmissive) material which transmits electromagnetic radiation of a wavelength between about 200 and about 900 nm. A support of choice for a particular element should be compatible with the intended mode of detection (transmission or reflectance spectroscopy). Useful supports can be prepared from paper, metal foils, polystyrene, polyesters [e.g. poly(ethylene terephthalate)], polycarbonates, cellulose esters (e.g. cellulose acetate), etc.

The porous spreading zone can be prepared from any suitable fibrous or non-fibrous material or mixtures of either or both as described in U.S. Pat. Nos. 4,292,272 (issued Sept. 29, 1981 to Kitajima et al), 3,992,158 (noted above), 4,258,001 (noted above) and 4,430,436 (issued Feb. 7, 1984 to Koyama et al) and Japanese Patent Publication 57(1982)-101760 (published June 24, 1982). It is desirable that the spreading zone be isotropically porous, meaning that the porosity is the same in each direction in the zone as caused by interconnected spaces or pores between particles, fibers, polymeric strands, etc.

The elements can have two or more discrete zones, either in the same layer or as superimposed layers. At least one of the zones is preferably a porous spreading zone. The other zones can be reagent zones or registration zones as those zones are known in the art, additional spreading zones, radiation-blocking or filter zones, subbing zones, barrier zones, etc. The zones are generally in fluid contact with each other, meaning that fluids, reagents and reaction products (e.g. color dyes) can pass or be transported between superposed regions of adjacent zones. Preferably, each zone is a separately coated layer.

In the elements of this invention, the components of the analytical composition are present in amounts which can be varied depending upon the same factors mentioned above in relation to solution assays. Generally, the leuco dye is present in an amount of at least about 20 mg/m$^2$. Peroxidase is present in an amount of at least about 10 I.U./m$^2$, and the phenol or aniline is present in an amount of at least about 2.5 mg/m$^2$. Optimal levels can be readily determined by one skilled in the art. The elements of this invention can also contain one or more other addenda commonly put in the elements for various manufacturing or operational advantages. Such addenda include or surfactants, buffers, solvents. hardeners and the like. These materials can be independently located in one or more of the zones of the element described above. In some embodiments, the phenol or aniline and leuco dye are in the same zone. In other embodiments, the phenol or aniline and peroxidase are in the same zone.

In using the element of this invention in an immunoassay, the labeled ligand analog and corresponding receptor can be incorporated into the element prior to use, or added at the time of the assay. In either case, they are generally present in the amounts noted above for the solution immunassay. Preferably, both are incorporated into the element prior to use. The labeled ligand analog may be incorporated into a separate water-soluble zone or layer in order to isolate it from the receptor. Such zones are described in copending and commonly assigned U.S. patent application Ser. Nos. 884,249 of Eikenberry filed on even date herewith and entitled BINDER COMPOSITION AND ANALYTICAL ELEMENT HAVING STABILIZED PEROXIDASE IN LAYER CONTAINING THE COMPOSITION, and 884,237 of Columbus et al filed on even date herewith and entitled ANALYTICAL ELEMENT HAVING WATER-SOLUBLE POLYMERS AND DETERMINATIONS USING SAME.

The receptor is preferably immobilized within the element prior to use, e.g. during manufacture. For example, it can be immobilized within the absorbent carrier material of the element. More particularly, it is immobilized within the porous spreading zone on a carrier material, such as glass or polymeric beads or other particles, resins, fibers and the like. One useful carrier material is a microorganism, such as *Saphylococcus aureus*. Alternatively, the porous absorbent carrier material can serve as the carrier material for immobilization.

A variety of different elements, depending on the method of assay, can be prepared in accordance with the present invention. Elements can be configured in a variety of forms, including elongated tapes of any desired width, sheets, slides or chips.

The assay of this invention can be manual or automated. In general, in using the dry elements, analyte determination is made by taking the element from a supply roll, chip packet or other source and physically contacting it with a sample (e.g. 1-200 μl) of the liquid suspected of containing the analyte so that the sample and reagents within the element become mixed. Such contact can be accomplished in any suitable manner, e.g. dipping or immersing the element into the sample or, preferably, by spotting the element by hand or machine with a drop of the sample with a suitable dispensing means.

After sample application, the element is exposed to any conditioning, such as incubation, heating or the like, that may be desirable to quicken or otherwise facilitate obtaining any test result.

The immunoassay of this invention is carried out in an element in such a manner that a complex is formed between the ligand and ligand analog and the receptor. Once complexation has taken place, any suitable separation technique can be used to vertically or horizontally separate complexed ligand analog from uncomplexed ligand analog.

In one embodiment, contact of the sample can be accomplished in such a manner that complexation of receptor and ligand and substantial horizontal separation of uncomplexed and complexed ligand occur during sample introduction. This contact can be carried out by hand or with a machine using a pipette or other suitable dispensing means to dispense the test sample. The sample of liquid can be applied to the element in a number of ways to effect horizontal separation. For example, a relatively large liquid sample (e.g. up to 200 μl) can be applied slowly (e.g. over at least about 5 seconds) in a continuous manner using a suitable dispensing means. Alternatively, the sample can be applied in small portions, e.g. as a series of two or more droplets (e.g. 0.1 to 1 μl) over a period of time (e.g. over at least about 5 seconds).

In another embodiment, separation can be accomplished by slowly adding a wash fluid after the liquid sample has been applied to the element. This wash causes uncomplexed materials to move away from the complexed materials.

The amount of ligand in the test sample is then determined by detecting the dye formed from oxidation of the leuco dye as a result of the reaction of peroxidase and substrate (e.g. change in reflection or transmission density). Either complexed or uncomplexed ligand can be determined in this manner.

In one embodiment noted above involving horizontal separation, the complexed ligand analog is measured in a finite area in the center of the contacted area. The amount of the ligand in the test sample is inversely proportional to the amount of ligand analog measured in that finite area. Generally, ligand analog measurement is carried out after from about 5 to about 500 seconds subsequent to applying the test sample to the element.

In the examples which follow, illustrating the practice of this invention, the materials used were obtained as follows: SURFACTANT 10G surfactant from Olin Corporation (Stamford, Conn., U.S.A.), TRITON X-100, X-165 and X-200E surfactants from Rohm and Haas (Philadelphia, Pa., U.S.A.), ZONYL FSN surfactant from DuPont (Wilmington, Del., U.S.A.), cholesterol oxidase from Upjohn Corp. (Kalamazoo, Mich., U.S.A.), cholesterol ester hydrolase from Enzyme Development Corp. (New York, N.Y., U.S.A.), peroxidase from Sigma Chemical Co. (St. Louis, Mo., U.S.A.) or Miles Laboratories (Elkhart, Ind., U.S.A.), and the remainder either from Eastman Kodak Company (Rochester, N.Y., U.S.A.) or prepared using standard procedures and readily available starting materials.

As used in the context of this disclosure and the claims, I.U. represents the International Unit for enzyme activity defined as one I.U. being the amount of enzyme activity required to catalyze the conversion of 1 micromole of substrate per minute under standard pH and temperature conditions for the enzyme.

EXAMPLE 1

Use of p-Methoxyphenol as Electron Transfer Agent to Increase Peroxidase Reaction Rate Potassium phosphate buffer (KP) solution (50μmolar, pH 6.5) was prepared from $K_2HPO_4$ (4.36 g/500 ml water) and $KH_2PO_4$ (3.41 g/500 ml water). A surfactant solution was prepared from TRITON X-165 (10% by weight) in 50 mmolar KP buffer.

A solution of 2-(3,5-dimethoxy-4-hydroxy-phenyl)-4,5bis(4-dimethylaminophenyl) imidazole leuco dye was prepared as follows: TRITON X-165 solution from above (28.6 ml), 50 mmolar KP buffer from above (171.4 ml) were purged with nitrogen and 0.2 g of leuco dye was added. The resulting mixture was stirred at 25° C. until solution was obtained (about 2 hours). This solution was diluted 1:19 with 200 mmolar KP buffer.

Test solutions were prepared by adding the reagents to a cuvette in the following order: 3 ml of leuco dye solution, 10 μl of 10 mmolar hydrogen peroxide in 200 mmolar KP buffer, p-methoxyphenol (various concentrations shown in Table I below) and 10 μl of peroxidase solution (7.58 mg enzyme having 165 purpurogallin units of activity/mg in 25 ml of 200 mmolar KP buffer).

Absorbances were determined at 670 nm using a standard spectrophotometer at 30° C. The resulting data, shown in Table I below as the change in absorbance (ΔA) after 1 minute, indicate an increased rate of leuco dye oxidation as catalyzed by peroxidase in the presence of p-methoxyphenol (PMP).

TABLE I

| PMP Concentration (Molar) | ΔA |
|---|---|
| 0 | 0.344 |
| $3.3 \times 10^{-8}$ | 0.369 |
| $8.3 \times 10^{-8}$ | 0.368 |
| $1.7 \times 10^{-7}$ | 0.400 |
| $3.3 \times 10^{-7}$ | 0.398 |
| $8.3 \times 10^{-7}$ | 0.467 |
| $1.7 \times 10^{-6}$ | 0.560 |
| $3.3 \times 10^{-6}$ | 0.652 |
| $8.3 \times 10^{-6}$ | 1.004 |
| $1.7 \times 10^{-5}$ | 1.240 |
| $3.3 \times 10^{-5}$ | 1.675 |
| $6.6 \times 10^{-5}$ | 2.314 |
| $9.9 \times 10^{-5}$ | 2.516 |

EXAMPLE 2

Use of 4'-Hydroxyacetanilide as Electron Transfer Agent in Increasing Peroxidase Reaction Rate The leuco dye solution used in Example 1 above was also used in this example. Test solutions were prepared by adding the reagents to a cuvette in the following order: leuco dye solution (3.0 ml), 10 μl of 10 mmolar hydrogen peroxide in 200 mmolar KP buffer, 4'-hydroxacetanilide (various concentrations shown in Table II below), and 10 ml of peroxidase (3.03 mg of enzyme having 165 purpurogallin units/mg in 50 ml of 200 mmolar KP buffer).

Absorbances were determined at 670 nm using a standard spectrophotometer at 30° C. The resulting data, shown in Table II below as the change in absorbance (ΔA) after 1 minute, indicate an increased rate of leuco dye oxidation as catalyzed by peroxidase in the presence of 4'-hydroxyacetanilide (4-HA).

TABLE II

| 4-HA Concentration (Molar) | ΔA |
|---|---|
| 0 | 0.167 |
| $8.3 \times 10^{-8}$ | 0.178 |
| $1.7 \times 10^{-7}$ | 0.200 |
| $3.3 \times 10^{-7}$ | 0.226 |
| $8.3 \times 10^{-7}$ | 0.265 |
| $1.7 \times 10^{-6}$ | 0.356 |
| $3.3 \times 10^{-6}$ | 0.535 |
| $8.3 \times 10^{-6}$ | 0.831 |
| $1.7 \times 10^{-5}$ | 1.108 |
| $3.3 \times 10^{-5}$ | 1.544 |
| $8.3 \times 10^{-5}$ | 1.900 |
| $1.7 \times 10^{-4}$ | 2.078 |
| $3.3 \times 10^{-4}$ | 2.104 |
| $6.6 \times 10^{-4}$ | 1.743 |
| $1.7 \times 10^{-3}$ | 1.461 |

EXAMPLE 3

Use of p, p'-Biphenol as Electron Transfer Agent to Increase the Reaction Rate of Peroxidase A solution of leuco dye was prepared from the following: 200 mmolar sodium phosphate buffer (pH 6.5), 100 mmolar glucose solution, sodium dodecylsulfate (5 g in 50 ml buffer), 0.05 g leuco dye in 50 ml of KP buffer, 0.05 molar dimedone and 1.25 mmolar hydrogen peroxide.

Test solutions were prepared by adding the reagents to a cuvette in the following order: 790 μl leuco dye solution, 200 μl of peroxidase (10 purpurogallin units/ml) and p, p'-biphenol (various amounts shown in Table III).

Absorbances were determined at 670 nm in a standard spectrophotometer at 30° C. The resulting data, shown in Table III as the change in absorbance (ΔA) after 1 minute, is the average of 4 readings and indicates an increased rate of leuco dye oxidation as catalyzed by peroxidase in the presence of p, p'-biphenol.

TABLE III

| p,p'-Biphenol Concentration (Molar) | ΔA |
|---|---|
| 0 | 0.004 |
| $10^{-5}$ | 0.382 |
| $2 \times 10^{-5}$ | 0.670 |
| $3 \times 10^{-5}$ | 0.886 |
| $5 \times 10^{-5}$ | 1.145 |
| $10^{-4}$ | 1.406 |

EXAMPLE 4

Determination of Digoxin Using an Analytical Element

This example is taken from copending and commonly assigned U.S. Ser. No. 884,249 of Eikenberry, noted above. This example illustrates the practice of this invention for the determination of digoxin.

An element of the present invention was prepared having the following format and components:

| | | |
|---|---|---|
| Spreading Layer | Poly(vinyltoluene-co-p-t-butylstyrene-co-methacrylic acid) beads | 50-300 g/m² |
| | Poly(methacrylate-co-2-acrylamido-2-methylpropane sulfonic acid-co-2-acetoacetoxyethyl methacrylate) adhesive | 1-10 g/m² |
| | *Staphylococcus aureus* coated with digoxin antibodies | 0.2-5 g/m² |
| | 2-(3,5-Dimethoxy-4-hydroxyphenyl)-4,5-bis(4-dimethylaminophenyl)imidazole leuco dye | 0.01-1 g/m² |
| | SURFACTANT 10G surfactant | 0.1-10 g/m² |
| Water-Soluble Layer | Poly(vinyl alcohol) | 0.1-10 g/m² |
| | ZONYL FSN surfactant | 0.01-1 g/m² |
| | Potassium phosphate buffer (pH 7) | 0.01-1 g/m² |
| | Digoxin peroxidase conjugate | $10^{-6}$-$10^{-4}$ g/m² |
| Reagent Layer | Gelatin (hardened) | 1-100 g/m² |
| | SURFACTANT 10G surfactant | 0.02-2 g/m² |
| | Potassium phosphate buffer | 0.05-5 g/m² |
| | α-Glycerol phosphate oxidase | 200-20,000 I.U./m² |
| | 4'-Hydroxyacetanilide | 0.01-1 g/m² |
| // | Poly(ethylene terephthalate) | // |
| // | Support | // |

Digoxin was determined using this element in the following manner. A series of test samples containing various amounts of the ligand, digoxin, were prepared in a buffered solution (pH 7). A 10 μl sample of each test sample was applied to the element prior to incubation for about 5 minutes at 37° C. At this time, a 10 μl sample of a wash fluid containing 100 mmole of α-glycerol phosphate was applied to the element over the area of the spreading layer contacted with the test sample to wash uncomplexed ligand analog horizontally away from complexed ligand analog, and to initiate the enzymatic reactions which produce a detectable dye. Complexed ligand analog was then determined by monitoring reflection densities at 670 nm in the center of the spotted area using a standard reflectometer. The rate of change in dye density was calculated from measurements taken between 60 and 120 seconds into the incubation. The Williams-Clapper transform (*J. Optical Soc. Am.*, 43, 595, 1953) was used to determine transmission density values from reflectance density values. The concentration of digoxin in the test fluid was observed to be inversely related to the rate of dye formation.

EXAMPLE 5

Determination of Phenytoin Using an Analytical Element

This example is taken from copending and commonly assigned U.S. Ser. No. 818,303, filed Jan. 13, 1986 by Danielson et al and entitled LABELED HYDANTOIN CONJUGATE AND ITS USE IN ANALYTICAL ELEMENT AND IMMUNOASSAY. This example illustrates the use of a phenol in an immunoassay for phenytoin.

An analytical element for the determination of phenytoin was prepared having the format and components illustrated below. Phenytoin is also known as diphenylhydantoin.

| | | |
|---|---|---|
| Spreading Layer | Polystyrene Beads (5-20 μm) coated with normal rabbit serum | 25-180 g/m² |
| | Poly(n-butyl acrylate-co-styrene-co-2-acrylamido 2-methylpropane sulfonic acid, sodium salt) [75:20:5 weight ratio] adhesive | 1-18 g/m² |
| | ZONYL FSN surfactant | 0.1-2.5 g/m² |
| | *S. aureus* coated with phenytoin anti-serum | 2-20 g/m² |
| Interlayer | Gelatin (hardened) | 1-20 g/m² |
| | ZONYL FSN surfactant | 0.1-2.5 g/m² |
| Reagent Layer | Gelatin (hardened) | 2-20 g/m² |
| | Leuco Dye* | 0.025-0.6 g/m² |
| | 5,5-dimethyl-1,3-cyclohexanedione | 0.01-0.5 g/m² |
| | Glucose | 0.9-6 g/m² |
| | 4'-Hydroxyacetanilide | 0.01-0.2 g/m² |
| | Sodium dodecyl sulfate | 0.5-10 g/m² |
| | Peroxidase | 1,000-50,000 I.U./m² |
| // | Poly(ethylene terephthalate) | // |
| // | Support | // |

*4,5-bis(4-dimethylaminophenyl)-2-(4-hydroxy-3,5-dimethoxyphenyl)imidazole

A series of test samples containing various amounts of phenytoin were prepared in a buffered solution comprising 0.01 molar 3-(N-morpholino) propanesulfonic acid buffer (pH 7), 0.15 molar sodium chloride and 0.05% rabbit gamma globulin. The concentrations of phenytoin in the test samples are listed in Table IV below.

The following labeled conjugate was used in the tests: 5-ethyl, 5-phenylhydantoin-valerate-glucose oxidase.

The label was mixed with each test sample and tested by spotting an 8 μl sample of the resulting mixture on the element and incubating the element for 7 minutes at 37° C. During the incubation, reflectance densities were monitored at 670 nm using a reflectometer. The rate of change in dye density was calculated from measurements taken between 60 and 120 seconds into the incubation. The Williams-Clapper transform (*J. Optical Soc. Am.*, 43, 595, 1953) was used to determine transmission density values from reflectance density values.

The results are shown in Table IV below. These data show that the observed rate, shown as the change in transmission density ($D_T$) with time, is inversely proportional to the concentration of phenytoin in the test sample. From dose response curves plotted using these data, a dynamic range of 0.155 was obtained.

TABLE IV

| Phenytoin Concentration (molar) | $D_T$/min. (Invention) |
|---|---|
| 0 | 0.307 |
| $10^{-8}$ | 0.289 |
| $10^{-7}$ | 0.267 |
| $10^{-6}$ | 0.225 |
| $10^{-5}$ | 0.188 |
| $10^{-4}$ | 0.154 |
| $2 \times 10^{-4}$ | 0.152 |

EXAMPLE 6

Determination of Cholesterol

This example illustrates the practice of this invention for the determination of cholesterol using an analytical element of the invention. This element was prepared having the following components and format:

| | | |
|---|---|---|
| Spreading/Reagent Layer | Barium sulfate | 70–140 g/m² |
| | Cellulose acetate | 6–12 g/m² |
| | Polyurethane resin | 0.5–1.5 g/m² |
| | Potassium phosphate buffer (pH 5.5–6.5) | 1–2 g/m² |
| | | 1–2 g/m² |
| | TRITON X-100 surfactant | 5–11 g/m² |
| | Peroxidase | 5,000–160,000 I.U./m² |
| | 4'-Hydroxyacetanilide | 0.01–1 g/m² |
| | Cholesterol oxidase | 2,000–4,000 I.U./m² |
| | Cholesterol ester hydrolase | 1,500–12,000 I.U./m² |
| | 2-(3,5-Dimethoxy-4-hydroxyphenyl)-4,5-bis(4-dimethylaminophenyl)imidazole | 0.8–3 g/m² |
| | 5,5-Dimethyl-1,3-cyclohexanedione | 0.2–0.8 g/m² |
| Subbing Layer | Poly(N—isopropylacrylamide) | 0.2–0.8 g/m² |
| Binder Layer | Gelatin (hardened) | 10–25 g/m² |
| | Potassium phosphate buffer | 0.1–2 g/m² |
| | TRITON X-200E surfactant | 0.005–0.02 g/m² |
| | SURFACTANT 10G surfactant | 0.005–0.01 g/m² |
| // | Poly(ethylene terephthalate) Support | // |

To evaluate this element, a series of cholesterol standards were prepared from bovine and human serum, varying in cholesterol concentration from 41 mg/dl to 876 mg/dl.

The element was spotted with 10 μl drops of these standards and the reflection densities were read at 540 nm and 37° C. using an EKTACHEM Clinical Chemistry Analyzer (Eastman Kodak Co., Rochester, N.Y.) using standard procedures. The reflection densities ($D_R$) obtained at the various concentrations are shown in Table V below.

TABLE V

| Cholesterol Concentration (mg/dl) | $D_R$, 540 nm, 37° C. |
|---|---|
| 41.0 | 0.522 |
| 93.0 | 0.756 |
| 144.0 | 0.926 |
| 198.0 | 1.060 |
| 268.0 | 1.205 |
| 308.3 | 1.288 |
| 392.0 | 1.387 |
| 438.0 | 1.456 |
| 441.8 | 1.526 |
| 533.0 | 1.589 |
| 649.0 | 1.691 |
| 876.0 | 1.770 |

EXAMPLE 7

Determination of Theophylline

An analytical element for the determination of theophylline was prepared having the following format and composition:

| | | |
|---|---|---|
| Spreading Layer | Polystyrene beads | 20–140 g/m² |
| | Poly(n-butyl acrylate-co-styrene-co-2-acrylamido-2-methylpropane sulfonic acid, sodium salt) (75:20:5 weight ratio) adhesive | 0.5–12 g/m² |
| | ZONYL FSN surfactant | 0.1–0.3 g/m² |
| Interlayer | Hardened gelatin | 1–10 g/m² |
| | ZONYL FSN surfactant | 0.05–0.2 g/m² |
| Reagent Layer | Hardened gelatin | 2–20 g/m² |
| | Glucose | 0.5–5 g/m² |

-continued

| | | |
|---|---|---|
| | 4'-Hydroxyacetanilide | 0.01–1 g/m² |
| | Peroxidase | 1,000–50,000 I.U./m² |
| | Sodium dodecyl sulfate | 1–8 g/m² |
| | 4,5-Bis(4-dimethyl aminophenyl)-2-(4-hydroxy-3,5-dimethoxyphenyl)imidazolone | 0.04–0.5 g/m² |
| | Dimedone | 0.01–0.5 g/m² |
| // | Poly(ethylene terephthalate) Support | // |

A series of solutions containing a theophylline-glucose oxidase conjugate, varying in concentration from $0.5 \times 10^{-8}$ molar to $8 \times 10^{-8}$ molar, were prepared with theophylline ($10^{-3}$ molar) and without theophylline. Samples (10 μl) of these solutions were then spotted onto a finite area of the spreading layer of the element described above.

After incubation at 37° C. of 2–3 minutes, the reflection density was measured in the center of the finite area of each element at 670 nm using a modified standard reflectometer. The Williams-Clapper transform (J. Optical Soc. Am. 43, 595, 1953) was used to determine transmission density values ($D_T$).

The resulting data in Table VI below show a difference in rate ($D_T$/min.) between the solutions with and without theophylline. The data indicate that this element is useful for the determination of theophylline (Theo).

TABLE VI

| Conjugate Concentration ($\times 10^{-8}$ Molar) | Rate ($D_T$/min.) | | |
|---|---|---|---|
| | No Theo | $10^{-3}$ molar Theo | Δ Rate |
| 0.5 | 0.025 | 0.012 | 0.013 |
| 1.0 | 0.045 | 0.020 | 0.025 |
| 2.0 | 0.082 | 0.045 | 0.037 |
| 4.0 | 0.162 | 0.080 | 0.082 |
| 8.0 | 0.220 | 0.155 | 0.065 |

The invention has been described in detail with particular reference to preferred embodiments thereof, but it will be understood that variations and modifications can be effected within the spirit and scope of the invention.

I claim:

1. An analytical composition comprising peroxidase or a peroxidase-labeled analog of an immunologically reactive ligand, an imidazole or triarylmethane leuco dye which is capable of providing a detectable dye in the presence of peroxidase and hydrogen peroxide, and a phenol or aniline electron transfer agent which is capable of reacting with hydrogen peroxide in the presence of peroxidase to provide an intermediate compound which has a higher oxidation potential than said leuco dye, said phenol or aniline electron transfer agent being p, p'-biphenol, 4'-hydroxyacetanilide, p-methoxyphenol, o-methoxyphenol, p-anisidine, p-hydroxy-N, N'-dimethyl-aniline or o-phenylenediamine.

2. The composition of claim 1 wherein said leuco dye is an imidazole derivative.

3. The composition of claim 2 wherein said imidazole derivative is a triarylimidazole.

4. The composition of claim 1 wherein said phenol or aniline electron transfer agent is 4'-hydroxy-acetanilide.

5. The composition of claim 1 further comprising an interactive composition which is capable of interacting with an analyte to provide hydrogen peroxide.

6. The composition of claim 1 comprising peroxidase and an analog of an immunologically reactive ligand labeled with an enzyme other than peroxidase.

7. The composition of claim 6 wherein said ligand analog comprises glucose oxidase.

8. An analytical element comprising an absorbent carrier material containing: peroxidase or a peroxidase labeled analog of an immunologically reactive ligand, an imidazole or triarylmethane leuco dye which is capable of providing a detectable dye in the presence of peroxidase and hydrogen peroxide, and a phenol or aniline electron transfer agent which is capable of reacting with hydrogen peroxide in the presence of peroxidase to provide an intermediate compound which has a higher oxidation potential than said leuco dye, said phenol or aniline electron transfer agent being p, p'-biphenol, 4'-hydroxyacetanilide, p-methoxyphenol, o-methoxyphenol, p-anisidine, p-hydroxy-N, N'-dimethyl-aniline or o-phenylenediamine.

9. An analytical element comprising a support having thereon a registration zone and a porous spreading zone, said element further comprising, independently in any of said zones, peroxidase or a peroxidase-labeled analog of an immunologically reactive ligand, an imidazole or triarylmethane leuco dye which is capable of providing a detectable dye in the presence of peroxidase and hydrogen peroxide, and a phenol or aniline electron transfer agent which is capable of reacting with hydrogen peroxide in the presence of peroxidase to provide an intermediate compound which has a higher oxidation potential than said leuco dye, said phenol or aniline electron transfer agent being p, p'-biphenol, 4'-hydroxyacetanilide, p-methoxyphenol, o-methoxyphenol, p-anisidine, p-hydroxy-N, N'-dimethyl-aniline or o-phenylenediamine.

10. The element of claim 9 comprising said peroxidase and phenol or aniline electron transfer agent in said registration zone.

11. The element of claim 9 wherein said zones are individually superposed layers.

12. The element of claim 9 further comprising an interactive composition which is capable of interacting with an analyte to provide hydrogen peroxide.

13. The element of claim 9 wherein said leuco dye is an imidazole derivative.

14. The element of claim 9 comprising peroxidase and an analog of an immunologically reactive ligand labeled with an enzyme other than peroxidase.

15. The element of claim 9 wherein said phenol or aniline electron transfer agent is 4'-hydroxyacetanilide and said leuco dye is 2-(3,5-dimethoxy-4-hydroxyphenyl)-4,5-bis(4-dimethylaminophenyl) imidazole.

16. The element of claim 9 further comprising a receptor for an immunologically reactive ligand.

17. A method for the determination of an analyte comprising the steps of:

A. contacting a sample of a liquid suspected of containing an analyte with:

peroxidase or a peroxidase-labeled analog of an immunologically reactive ligand, an imidazole or triarylmethane leuco dye which is capable of providing a detectable dye in the presence of peroxidase and hydrogen peroxide, and a phenol or aniline electron transfer agent which is capable of reacting with hydrogen peroxide in the presence of peroxidase to provide an intermediate compound which has a higher oxidation potential than said leuco dye, said phenol or aniline electron transfer agent being p, p'-biphenol, 4'-hydroxyacetanilide, p-methoxyphenol, o-methoxyphenol, p-anisidine, p-hydroxy-N, N'-dimethyl-aniline or o-phenylenediamine, and B. determining said detectable dye as a result of the presence of said analyte.

18. The method of claim 17 for the determination of an analyte other than hydrogen peroxide wherein said liquid sample is also contacted with an interactive composition which is capable of reacting with said analyte to provide hydrogen peroxide.

19. The method of claim 17 for the determination of an immunologically reactive ligand carried out in the presence of a receptor for said ligand.

20. The method of claim 19 carried out with a peroxidase-labeled analog of said immunologically reactive ligand.

21. The method of claim 19 carried out with peroxidase and an analog of said immunologically reactive ligand labeled with an enzyme other than peroxidase.

22. The method of claim 17 wherein said phenol or aniline electron transfer agent is 4'-hydroxyacet-anilide.

23. The method of claim 17 carried out with an analytical element comprising an absorbent carrier material containing said peroxidase or peroxidase-labeled analog, said imidazole or triarylmethane leuco dye and said electron transfer agent.

24. The method of claim 17 for the determination of glucose, triglycerides, uric acid, cholesterol or creatine kinase.

25. A leuco dye composition comprising an imidazole or triarylmethane leuco dye which is capable of providing a detectable dye in the presence of peroxidase and hydrogen peroxide, and a phenol or aniline electron transfer agent which is capable of reacting with hydrogen peroxide to provide an intermediate compound which has a higher oxidation potential than said leuco dye, said phenol or aniline electron transfer agent being p, p'-biphenol, 4'-hydroxyacetanilide, p-methoxyphenol, o-methoxyphenol, p-anisidine, p-hydroxy-N, N'-dimethylaniline or o-phenylenediamine.

26. The leuco dye composition of claim 25 wherein said electron transfer agent is 4'-hydroxyacetanilide.

* * * * *